US005550172A

United States Patent [19]

Regula et al.

[11] Patent Number: 5,550,172
[45] Date of Patent: Aug. 27, 1996

[54] UTILIZATION OF BIOCOMPATIBLE ADHESIVE/SEALANT MATERIALS FOR SECURING SURGICAL DEVICES

[75] Inventors: Donald W. Regula, Belle Mead; Kevin Cooper, Warren; Michael F. Bregen, Milford; Shawn T. Huxel, Lakehurst, all of N.J.; Daniel C. Rosenman, San Mateo, Calif.

[73] Assignee: Ethicon, Inc., Somerville, N.J.

[21] Appl. No.: 385,015

[22] Filed: Feb. 7, 1995

[51] Int. Cl.$^6$ .............. C08K 5/10; A61B 17/56; A61B 17/58; C01B 15/16
[52] U.S. Cl. .............. 523/118; 606/76; 606/77; 528/354; 423/305; 423/308; 423/309; 423/311
[58] Field of Search .............. 523/118; 606/76, 606/77; 528/354, 363; 524/436; 423/305, 308, 309, 311

[56] References Cited

U.S. PATENT DOCUMENTS

| | | | |
|---|---|---|---|
| Re. 33,161 | 2/1990 | Brown et al. | 423/308 |
| Re. 33,221 | 5/1990 | Brown et al. | 423/308 |
| 3,995,641 | 12/1976 | Kronenthal et al. | 128/335 |
| 4,612,053 | 9/1986 | Brown et al. | 706/35 |
| 4,668,295 | 5/1987 | Bajal | 106/35 |
| 4,880,610 | 11/1989 | Constanz | 423/305 |
| 4,902,649 | 2/1990 | Kimura et al. | 501/1 |
| 5,053,212 | 10/1991 | Constanz et al. | 423/305 |
| 5,178,845 | 1/1993 | Constanz et al. | 423/305 |
| 5,218,035 | 6/1993 | Liu | 524/414 |
| 5,223,029 | 6/1993 | Oonishi et al. | 106/35 |
| 5,238,491 | 8/1993 | Sugihara et al. | 106/35 |
| 5,281,265 | 1/1994 | Liu | 106/35 |
| 5,296,026 | 3/1994 | Monroe et al. | 106/35 |
| 5,328,687 | 7/1994 | Leung et al. | 424/78.35 |

FOREIGN PATENT DOCUMENTS

| | | | |
|---|---|---|---|
| 0298501 | 7/1988 | European Pat. Off. | A61K 6/06 |
| 0520690A2 | 6/1992 | European Pat. Off. | A61K 6/033 |
| 0617973A1 | 3/1994 | European Pat. Off. | A61L 25/00 |
| 3273679 | 11/1988 | Japan | 523/118 |

OTHER PUBLICATIONS

Development of Self–Setting Calcium Phosphate Cements, The Centennial Memorial Issue of The Ceramic Society of Japan, pp. 954–964.

Coral Chemistry Leads to Human Boan Repair, Science Vo. 267, 24 Mar. 1955, p. 1772.

*Primary Examiner*—Paul R. Michl
*Assistant Examiner*—LaVonda R. DeWitt
*Attorney, Agent, or Firm*—Hal Brent Woodrow

[57] ABSTRACT

A process for enhancing the security of implantable surgical devices secured to bone tissue comprising implanting in bone tissue a surgical device with a biocompatible adhesive and/or sealant selected from the group consisting of: p1 (a) a material made from monomers of the formula:

$$CHR^1=CX^1Y^1$$

wherein $X^1$ and $Y^1$ are each strong electron withdrawing groups, and $R^1$ is hydrogen or, provided that $X^1$ and $Y^1$ are both cyano groups, a $C_1$-$C_4$ alkyl group;

(b) a semi-crystalline aliphatic poly(ester) of the formula:

$$[-O-R^{11}-C(0)-]_y,$$

wherein $R^{11}$ is selected from the group consisting of $-CR^{12}H-$, $-(CH_2)_3-O-$, $-CH_2-CH_2-O-CH_2-$, $CR_{12}H-CH_2$, $-(CH_2)_4-$, $-(CH_2)_z-O-C(O)-$ and $-(CH_2)_z-C(O)-CH_2-$; $R^{12}$ is hydrogen or methyl; z is an integer in the range of from 1 to 7 and y is an integer in the range of from about 10 to about 20,000; and (c) a slurry of water and a calcium containing compounds with the general formula:

$$M^{2+}{}_{10-n}N^{1+}{}_{2n}(WO_4{}^{3-})_6mU^{2-}$$

where n is an integer from 1 to 10, and m is 2 when x is 1, or m is 1 when x is 2, M and N are alkali or alkaline earth metals; $WO_4$ is an acid radical and w is phosphorus, vanadium, sulfur, silicon, or is substituted in whole or part with carbonate ($CO_3{}^{2-}$); and U is a halide, hydroxide, or carbonate; provided in an amount effective to increase the amount of force necessary to remove the implanted surgical device. Additionally provided is a surgical device that is at least partially coated with at least one biocompatible adhesive and/or sealant.

12 Claims, No Drawings

UTILIZATION OF BIOCOMPATIBLE ADHESIVE/SEALANT MATERIALS FOR SECURING SURGICAL DEVICES

FIELD OF THE INVENTION

This invention relates to securing surgical repair devices to tissue, more specifically this invention relates to securing surgical devices such as screws, plates, bone pins and anchors to bone tissue.

BACKGROUND OF THE INVENTION

In orthopedic surgery it is often necessary to reattach cartilage and ligaments to skeletal bones with surgical pins, screws or anchors. For example, metallic suture anchors are currently used to facilitate cartilage or ligament reattachment. In these procedures a hole is drilled into the skeletal bone. A suture anchor, attached to a suture, is then inserted into the hole in a manner that allows the anchor to engage the sides of the hole and be held in place. The suture is then used to secure the torn cartilage or ligament to the bone. However, sometimes during or after the healing process these anchors fail to remain in place and must be removed to avoid harm to the patient.

Recently, absorbable suture anchors have been proposed as a replacement for metallic suture anchors. The perceived advantage of an absorbable anchor over the metallic anchor is that after the healing process for the cartilage or ligament is complete the anchor will be absorbed by the patient's body and disappear. However, most bioabsorbable materials are not strong enough to dig into bone tissue. Therefore, bioabsorbable bone anchors tend to have less resistance to being pulled out of the location in which it is secured.

Thus, it would be a significant contribution to the art to provide a method to enhance the secure placement of implantable surgical devices in patients. Additionally, it would be advantageous if a method could be developed to enhance the resistance to removal of bioabsorbable surgical implantable devices.

SUMMARY OF THE INVENTION

We have discovered a process for enhancing the security of implantable surgical devices secured to bone tissue comprising implanting a surgical device with a biocompatible adhesive and/or sealant provided in an amount effective to increase the security of the implanted surgical device.

In another embodiment of the present invention we have also provided an implantable surgical device comprising an implantable surgical device coated with a biocompatible adhesive or sealant.

DETAILED DESCRIPTION OF THE INVENTION

The present invention provides a process for using a surgical device that improves the security and placement of the surgical device in a mammalian body. Also described is an implantable surgical device which has been coated with a biocompatible adhesive or sealant in an amount sufficient to facilitate the placement of the surgical device in the desired location in a patient. Suitable surgical devices which may benefit from having an adhesive or sealant coating include but are not limited to surgical screws, pins, plates, anchors, rods, clamps, clips, staples, rivets, hooks, buttons, snaps and the like.

These surgical devices may be made from a biocompatible material using conventional fabrication methods. The clips can be composed of various biocompatible metals, e.g. titanium and tantalum, and polymeric materials. Preferred bioabsorbable polymeric materials include homopolymers and copolymers of epsilon-caprolactone, glycolide, lactide, para-dioxanone, and trimethylene carbonate. Preferred nonabsorbable polymers include nylons, polyesters and polypropylene. All these materials have been demonstrated to be biologically acceptable when used as sutures or other implantable medical devices.

The preferred means for fabricating surgical devices from polymeric materials is to inject a suitable polymer melt into an appropriately designed mold at process conditions conventionally employed for such polymer systems. After the polymer melt cools, the molded polymer shaped in the mold to meet the design criteria of the device can be readily released from the mold.

One class of suitable biocompatible adhesives or sealants that can be used in the practice of the present invention include materials made from monomers of the formula:

$$CHR^1{=}CX^1Y^1 \qquad (I)$$

wherein $X^1$ and $Y^1$ are each strong electron withdrawing groups, and $R^1$ is hydrogen or, provided that $X^1$ and $Y^1$ are both cyano groups, a $C_1$–$C_4$ alkyl group. Examples of monomers within the scope of formula (I) include α-cyanoacrylates, vinylidene cyanides, $C_1$–$C_4$ alkyl homologues of vinylidene cyanides, dialkyl methylene malonates, acylacrylonitriles, vinyl sulfinates, and vinyl sulfonates of the formula $CH_2{=}CX^2Y^2$ wherein $X^2$ is $SO_2R^2$ or $-SO_3R^2$ and $Y^2$ is $-CN$, $COOR^2$, $COCH_3$, $-SO_2R^2$ or $-SO_3R^2$ and $R^2$ is hydrogen or an alkyl group.

Preferred monomers of formula (I) for use in this invention are alpha-cyanoacrylates. These monomers are known in the art and have the formula

$$CHR^3{=}C\begin{matrix}CN\\COOR^4\end{matrix} \qquad (II)$$

wherein $R^3$ is hydrogen and $R^4$ is a hydrocarbon or substituted hydrocarbon group; a group having the formula $-R^5-O-R^6-O-R^7$, wherein $R^5$ is a 1,2-alkylene group having 2–4 carbon atoms, $R^6$ is an alkylene group having 2–4 carbon atoms, and $R^7$ is an alkyl group having 1–6 carbon atoms; or a group having the formula:

$$-R^8-\underset{\underset{O}{\|}}{C}-O-R^9 \qquad (III)$$

wherein $R^8$ is

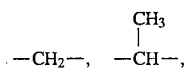

$$-CH_2-,\ -\underset{\underset{CH_3}{|}}{CH}-,$$

or $-C(CH_3)_2-$ and $R^9$ is an organic radical.

Examples of suitable hydrocarbon and substituted hydrocarbon groups include straight chain or branched chain alkyl groups having 1–16 carbon atoms; straight chain or branched chain $C_1$–$C_{16}$ alkyl groups substituted with one or more biologically compatible substituents such as an acyloxy group, an alkoxy group, an aryloxy group, a haloalkyl group, a halogen atom, a dialkylamino group, an alkylarylamino group, or a cyano group; straight chain or branched chain alkenyl groups having 2 to 16 carbon atoms; straight chain or branched chain alkynyl groups having 2 to 12 carbon atoms; cycloalkyl groups; arylalkyl groups; alkylaryl groups and aryl groups In the cyanoacrylate monomer of formula (II), $R^4$ is preferably an alkyl group having 1–10 carbon atoms or a group having the formula $-AOR^{10}$, wherein A is a divalent straight or branched chain alkylene or oxyalkylene radical having 2–8 carbon atoms, and $R^{10}$ is a straight or branched alkyl radical having 1–8 carbon atoms. Examples of groups represented by the formula $-AOR^{10}$ include 1-methoxy-2-propyl, 2-butoxy ethyl, isopropoxy-ethyl, and 2-ethoxy ethyl.

The most preferred alpha-cyanoacrylate monomers used in this invention are methyl alpha-cyanoacrylate, butyl alpha-cyanoacrylate, octyl alpha-cyanoacrylate, 1-methoxy-2-propyl cyanoacrylate, 2-butoxy ethyl cyanoacrylate, and isopropoxy-ethyl cyanoacrylate.

The alpha-cyanoacrylates of formula (II) wherein $R^4$ is a hydrocarbon or substituted hydrocarbon group can be prepared according to methods known in the art. Reference is made, for example, to U.S. Pat. Nos. 2,721,858 and 3,254,111, each of which is hereby incorporated by reference herein. For example, the alpha-cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The alpha-cyanoacrylate monomers prepared with low moisture content and essentially free of impurities are preferred for biomedical use.

The alpha-cyanoacrylates of formula (II) wherein $R^4$ is a group having the formula $R^5-O-R^6-O-R^7$ can be prepared according to the method disclosed in U.S. Pat. No. 4,364,876 (Kimura et al.), which is hereby incorporated by reference herein. In the Kimura et al. method, the alpha-cyanoacrylates are prepared by producing a cyanoacetate by esterifying cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The alpha-cyanoacrylates of formula (II) wherein $R^4$ is a group having the formula

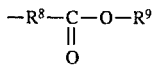

can be prepared according to the procedure described in U.S. Pat. No. 3,995,641 (Kronenthal et al.), which is hereby incorporated by reference herein. In the Kronenthal et al. method, such alpha-cyanoacrylate monomers are prepared by reacting an alkyl ester of an alpha-cyanoacrylic acid with a cyclic 1,3-diene to form a Diels-Alder adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct.

Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Another type of biocompatible adhesives or sealant that may be used in the practice of the present invention are copolymers of formula (I) or one monomer of formula (I) and a monomer of the formula:

wherein $X^1$ and $Y^1$ are as described for formula (I) and Z is $-CH=CH_2$. Examples of monomers of formula (IV) include cyanopentadienoates and alpha-cyanoacrylates of the formula:

wherein Z is $-CH=CH_2$ and $R^4$ is as defined above. The monomers of formula (IV) wherein $R^4$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4,4-dienoic acid esters is disclosed, for example, in U.S. Pat. No. 3,554,990, which is hereby incorporated by reference herein.

Optionally, a biocompatibilizing agent may be added to the cyanoacrylate adhesive such as are disclosed in U.S. Pat. No. 5,328,687, hereby incorporated by reference.

Suitable bioabsorbable sealants include semi-crystalline aliphatic ester homopolymers, and copolymers made from polymers of the formula:

wherein $R^{11}$ is selected from the group consisting of $-CR^{12}H-$, $-(CH_2)_3-O-$, $-CH_2-CH_2-O-CH_2-$, $CR^{12}H-CH_2$, $-(CH_2)_4-$, $-(CH_2)_z-O-C(O)-$ and $-(CH_2)_z-C(O)-CH_2-$; $R^{12}$ is hydrogen or methyl; z is an integer in the range of from 1 to 7; and y is an integer in the range of from about 10 to about 20,000.

Many nontoxic bioabsorbable aliphatic ester polymers that are semi-crystalline solids at room temperature, may be used in the present invention. The polymers of this invention are generally characterized as being solids at body temperature (37° C.) and preferably will be melt at temperatures of less than 60° C. Suitable bioabsorbable polymers include solid poly(ε-caprolactone), poly(p-dioxanone), or poly(trimethylene carbonate) homopolymers and copolymers of ε-caprolactone and trimethylene carbonate. Copolymers of ε-caprolactone should be composed of from about 100 mole percent to about 70 mole percent and preferably from 95 mole percent to 85 mole percent of ε-caprolactone repeating units with the remainder of the polymer being a plurality of second lactone repeating units. The second lactone repeating units will be selected from the group consisting of glycolide repeating units, lactide repeating units, 1,4-dioxanone repeating units, 1,4-dioxepan-2-one repeating units, 1,5-dioxepan-2-one repeating units, trimethylene carbonate repeating units, and combinations thereof. Preferred are copolymers of ε-caprolactone that are semicrystalline solids at body temperature. The solid polymers of trimethylene carbonate should be composed of from in the range of from about 1 to about 20 mole percent or from about 100 to about 80 mole percent of trimethylene carbonate with the remainder of the copolymer being composed of a plurality of lactone repeating units selected from the group consisting of glycolide repeating units, lactide repeating units, p-dioxanone repeating units, ε-caprolactone repeating units, and combinations thereof.

It is preferred for the trimethylene carbonate copolymers to have crystalline regions formed by the second lactone repeating units wherein the crystalline regions provide at least 5 percent crystallinity to the final copolymer. The solid polymers may be linear, branched, or star branched; block copolymers or terpolymers; segmented block copolymers or terpolymers. These polymers will also be purified to substantially remove unreacted monomers which may cause an inflammatory reaction in tissue. The most preferred polymers for use as the adhesive/sealant are semicrystalline polymers selected from the group consisting of poly(ε-caprolactone), poly(ε-caprolactone-co-trimethylene carbonate), poly(ε-caprolactone-co-lactide), poly(ε-caprolactone-co-p-dioxanone), and poly(ε-caprolactone-co-glycolide). The mole percent of ε-caprolactone repeating units in these polymers should be in the range of from 100 to about 80 mole percent and preferably in the range of from 95 to 85 mole percent. Most preferably these polymers will be statistically random copolymers.

The polymers used as the adhesive/sealant should have an inherent viscosity as determined in a 0.1 g/dL solution of hexafluoroisopropanol (HFIP) at 25° C. ranging from about 0.1 dL/g to about 2.0 dL/g, preferably from about 0.15 dL/g to about 1.5 dL/g, and most preferably from 0.2 dL/g to 1.0 dL/g. A polymer with an inherent viscosity below 0.1 dL/g may fail to crystallize at room temperature, and a polymer with an inherent viscosity above 2.0 dL/g may make the polymer have too high of a melting point.

The aliphatic poly(ester)s-are generally prepared by a ring opening polymerization of the desired proportions of one or more lactone monomers in the presence of an organometallic catalyst and an initiator at elevated temperatures. The organometallic catalyst is preferably a tin-based catalyst, e.g. stannous octoate, and is present in the monomer mixture at a molar ratio of 10 monomer to catalyst ranging from about 15,000/1 to about 80,000/1. The initiator is typically an alkanol (such as 1-dodecanol), a polyol (such as 1,2-propanediol, 1,3-propanediol, diethylene glycol, or glycerol, poly(ethylene glycol)s, poly(propylene glycol)s and poly(ethylene-co-propylene glycol)s), a hydroxyacid, or an amine, and is present in the monomer mixture at a molar ratio of monomer to initiator ranging from about 100/1 to about 5000/1. The polymerization is typically carried out at a temperature range from about 80° to about 220° C., preferably 160° to 190° C., until the desired molecular weight and viscosity are achieved.

The aliphatic polyesters described above will be solids at room temperature but may be heated to provide a putty like or liquid material that may be applied as a sealant to support surgical devices or to secure a surgical device. In one embodiment of the present invention, the aliphatic polyester would be heated to its melting point and applied to the desired location before it resolidified. In this embodiment, if a bone pin were inserted in a hole drilled in bone tissue, melted polyester would be poured into the hole before or after the pin was inserted to help secure the bone pin in the bone tissue. Alternatively, the aliphatic polyester could be heated until it softens and then used as a putty and placed at the desired location and act as a filler.

Other suitable bioabsorbable sealants include calcium containing compounds with the general formula:

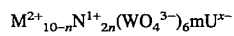

$$M^{2+}{}_{10-n}N^{1+}{}_{2n}(WO_4{}^{3-})_6 mU^{x-}$$

where n is an integer from 1 to 10, and m is 2 when x is 1, or m is 1 when x is 2, M and N are alkali or alkaline earth metals, preferably calcium, magnesium, sodium, zinc, and potassium. $WO_4$ is an acid radical, where W is preferably phosphorus, vanadium, sulfur or silicon, or is substituted in whole or part with carbonate ($CO_3{}^{2-}$). U is an anion, preferably halide, hydroxide, or carbonate.

Most preferred are calcium containing sealants selected from the group consisting of mono-, di-, octa-, α-tri-, β-tri-, or tetra-calcium phosphate, hydroxyapatite, fluorapatite, calcium sulfate, calcium fluoride and mixtures thereof.

The calcium containing sealants can also contain a bioactive glass comprising metal oxides such as calcium oxide, silicon dioxide, sodium oxide, phosphorus pentoxide, and mixtures thereof, and the like. The calcium containing sealants will preferably have a particle size of about 10 microns to about 1000 microns, and more preferably about 100 microns to about 500 microns.

The calcium containing sealants will generally be applied in an aqueous slurry. The amount of calcium containing material in the slurry will generally be in the range from about 10 weight percent to about 90 weight percent. The slurry will preferably be retained in place at the desired location until it solidifies or develops a putty like consistency.

The adhesive and/or sealant may be applied to at least one surface of the medical device that is to be contacted with the bone tissue or applied to the site where the surgical device is to be secured. For example, when a bone pin or anchor is placed in a hole drilled in bone tissue the pin or anchor surfaces that will contact the bone tissue will be coated with adhesive and placed in intimate contact with the bone tissue. The adhesive will then adhere to the device and the bone and enhance the security of the pin or anchor in the hole. Alternatively, the adhesive may be applied to the site where the surgical device is to be secured and the surgical device applied thereafter in an appropriate time so that the adhesive or sealant can set. If a sealant is used the sealant may serve as a filling and support agent for the medical device. For example, when using a bone plate with multiple openings for fasteners (such as screws), the sealant would be applied to the surface to contact the bone to provide a putty like base on which to mount the bone plate on to simplify installation of the bone plate.

Those skilled in the art will readily be able to determine the appropriate amount of adhesive and/or sealant to apply in a given surgical application. Similarly, the amount of an adhesive and/or sealant to be applied to a surgical device before implantation will be a discretionary matter depending on the operation and the specific circumstances of the operation.

The adhesives and/or sealants of the present invention will generally be applied in a liquid form. The adhesive and/or sealant will generally be applied through a small diameter delivery device such as a syringe, with or without mechanical assistance, a caulking gun, a soft-sided tube, and the like.

The following nonlimiting examples are provided to illustrate the practice of the present invention.

EXAMPLE 1

Synthesis of the Anthracene Adduct of Dimethyl Methylidene Malonate. 178.0 grams (1.00 mol) of powdered anthracene, 60.0 grams (2.00 mol) of powdered paraformaldehyde, 132.0 grams (1.00 mol) of dimethyl malonate, 10.0 grams (50 mmol) of cupric acetate monohydrate, 225 mL of glacial acetic acid, and 450 mL of xylene were added to a two liter, three necked, round bottom flask. In the exhaust hood, the flask was immersed into an oil bath and secured with a clamp. A mechanical stirrer, a stainless steel thermocouple connected to a thermowatch which controlled the immersion heater, and a water cooled distillation apparatus were then installed. The still was connected to a dry nitrogen gas line via a Firestone valve. The contents of the reaction flask were heated to 100° C. for 18 hours; then, the pot temperature was raised until the azeotropic mixture of acetic acid, water, and xylene started to distill out. The oil bath temperature ranged 125° C. to 145° C. during the distillation. The still head temperature varied from 95° 1 C. to 110° C. When most of the solvents were removed, the resulting suspension was allowed to cool down to room temperature. The residue was dissolved in chloroform, and in portions, transferred into a separatory funnel, washed with an equal volume of saturated ammonium chloride solution, washed with saturated sodium chloride solution, dried over anhydrous magnesium sulfate, and suction filtered. The filtrate was transferred into a round bottom flask and the chloroform removed by evaporation. The crude product [305 grams; 95% yield, but impure] was then recrystallized from xylene [1 gram/2 mL] using activated charcoal at −5° C. 228 grams of recrystallized adduct were collected [75% recovery; 71% yield overall, although the material is still contaminated with small amounts of anthracene]. The material was recrystallized again to produce about 188 grams of doubly recrystallized adduct [82% recovery; 58% yield overall; still contained some anthracene]. The material was recrystallized again yielding 158 grams of triply recrystallized material [84% recovery; 49% overall yield]. The crystals were isolated by suction filtration, washed with methanol, and vacuumed dried at 50° C. after each recrystallization.

EXAMPLE 2

Synthesis of Dimethyl Methylidene Malonate (DMMM). 500 grams of mineral oil, 120.0 grams (373 mmol) of the anthracene adduct of dimethyl methylidene malonate, 64.9 grams (375 mmol) of N-phenylmaleimide, and 050 grams (3.5 mmol) of phosphorous pentoxide were added to a silanized, flame dried, one liter round bottom flask containing a magnetic stirring bar. This mixture was degassed on a vacuum manifold overnight. Then, a silanized distillation head and fraction cutter were installed, and the flask immersed in an oil bath already set at 225° C. under a nitrogen atmosphere. After fifteen minutes, a yellow solution was obtained. One hour later, the oil bath was removed and the contents of the flask were allowed to cool down to 50° C. High vacuum was then applied to the reaction system. A pressure of around 450 microns was typical in the beginning of the distillation, and the pressure fell to around 300 microns by the end of the distillation. Once the system stabilized at low pressure, the dimethyl methylidene malonate distilled over between 50° C. and 55° C. [the oil bath temperature ranged from 50° C. to around 70° C.]. 31.0 grams of dimethyl methylidene malonate were collected in the middle fraction [58% yield;>99 mole % pure by NMR spectroscopy].

EXAMPLE 3 synthesis of Poly[ε-caprolactone] (PCL). In the glove box, 1°μL (40 μmol) of a 0.33M stannous octoate solution in toluene, 2.3 mL (24 mmol) of distilled diethylene glycol, and 205.3 grams (1.8 mol) of distilled ε-caprolactone were transferred into a silanized, flame dried, 500 mL, round bottom flask equipped with a stainless steel mechanical stirrer and a nitrogen gas blanket. The reaction flask was immersed in an oil bath already set at 75° C. After fifteen minutes, a clear solution was obtained and then the oil bath temperature was raised to 190° C. for 19 hours. The stirrer blade was removed, and the polymer melt was allowed to cool down to room temperature in an inert atmosphere. After about two hours, the polymer started to crystallize and became opaque. The polymer was isolated by wrapping the flask in aluminum foil, freezing the flask in liquid nitrogen, and removing the broken glass. Then, the frozen polymer was ground on a Wiley mill and sieved through a screen. 35.2 grams of a fine powder were saved; 161.8 grams of the coarse grounds were vacuum dried at 40° C. for 12 hours. 160.9 grams of devolatized PCL were collected. The PCL was vacuum dried again under the same conditions without any weight loss. The inherent viscosity was measured in chloroform at 25° C. and found to be 0.3 dL/g [c=0.10 g/dL]. The number average molecular weight was 9,000 g/mol and the weight average molecular weight was 16,000 g/mol as determined by gel permeation chromatography in HFIP using PMMA standards. The monomer conversion was 97.6 mole percent as determined by 300 MHz $^1$H NMR spectrum in HFAD/$C_6D_6$; 2.4 mole percent unreacted monomer was also detected. The polymer melted between 60° C. and 65° C. using a Fisher-Johns apparatus.

In the glove box, 25 grams of PCL and 0.25 grams of sucrose [a nucleating agent] were added to a silanized, flame dried, 100 mL, round bottom flask equipped with a stainless steel mechanical stirrer and a nitrogen gas blanket. The reaction flask was immersed in an oil bath set at 125°C. After the PCL had melted, the mixture was blended for one hour and then allowed to cool down to room temperature under an inert atmosphere. The polymer was isolated by wrapping the flask in aluminum foil, freezing the flask in liquid nitrogen, and removing the broken glass. The frozen polymer was crushed and vacuum dried at room temperature overnight and then stored under nitrogen gas until used in the bone pin study described below.

EXAMPLE 4

Bone Pin Pullout Force Measurements. Materials and Methods: Rabbit femurs were cleaned and frozen. They were defrosted before testing and allowed to warm up to 37° C. A hole was drilled in the femoral condyle with a 2.7 mm drill bit. Bone pins made of poly[glycolic acid] having a nominal diameter of 2.8 mm were roughened with sand paper to improve adhesion and were inserted into the femoral condyle with no adhesive, with Vetbond (n-butyl cyanoacrylate), dimethyl methylene malonate (DMMM) from Example 2 and with low molecular weight poly[ε-caprolactone] (PCL) from Example 3. The cure time was one minute for the Vetbond and DMMM and thirty minutes for the low molecular weight PCL. Mechanical testing was conducted on an Instron model 1122 tensile tester at a cross head speed of 0.5 inches per minute. The femur was held in the bottom fixture, and the bone pin was pulled out by the upper fixture. The force was measured and the maximum force recorded.

Results: The pullout force data are summarized in Table 1. These data clearly show that the average pullout force increased significantly when an adhesive was used; the increase in pullout strength varied from 4 to 11 times that of the force needed to remove the bone pin without any glue being applied.

TABLE 1

| | Pullout Strengths | | | |
| | Pullout Strengths (kg) | | | |
| Test | Bone Pin Only | Vetbond | DMMM | PCL |
|---|---|---|---|---|
| 1 | 0.661 | 6.95 | 3.43 | 2.3 |
| 2 | 0.765 | 8.35 | 7.41 | 2.94 |
| 3 | — | 9.82 | 6.79 | 2.19 |
| 4 | — | 5.66 | 2.27 | 3.41 |
| Average | 0.71 | 7.70 | 4.98 | 2.71 |

We claim:

1. A process for enhancing the security of implantable surgical devices secured to bone tissue consisting essentially of securing a surgical device with a biocompatible adhesive and/or sealant selected from the group consisting of:

(a) a bioabsorbable semi-crystalline aliphatic poly(ester) of the formula:

$$[-O-R^{11}-C(O)-]_y,$$

wherein $R^{11}$ is selected from the group consisting of $-CR^{12}H-$, $-(CH_2)_3-O-$, $-CH_2-CH_2-O-CH_2-$, $CR^{12}H-CH_2$, $-(CH_2)_4-$, $-(CH_2)_z-O-C(O)-$ and $-(CH_2)_z-C(O)-CH_2-$; $R^{12}$ is hydrogen or methyl; z is an integer in the range of from 1 to 7 and y is an integer in the range of from about 10 to about 20,000; and (b) a slurry of water and a calcium containing compound with the general formula:

$$M^{2+}{}_{10-n}N^{1+}{}_{2n}(WO_4{}^{3-})_6mU^{x-}$$

where n is an integer form 1 to 10, and m is 2 when x is 1, or m is 1 when x is 2, M and N are alkali or alkaline earth metals; $WO_4$ is an acid radical and W is phosphorus, vanadium, sulfur, silicon, or is substituted in whole or part with carbonate ($CO_3{}^{2-}$); and U is a halide hydroxide, or carbonate; provided in an amount effective to increase the amount of force necessary to remove the implanted surgical device.

2. The process of claim 1 wherein the sealant and/or adhesive is applied to the site where the implantable surgical device is to be secured.

3. The process of claim 1 wherein the surgical device is selected from the group consisting of screws, pins, plates, anchors, rods, clamps, clips, staples, rivets, hooks, buttons and snaps.

4. The process of claim 1 wherein the surgical device is made of a bioabsorbable polymeric material.

5. The process of claim 1 wherein the adhesive and/or sealant is a bioabsorbable semi-crystalline aliphatic poly(ester) homopolymer selected from the group consisting of poly(ε-caprolactone), poly(p-dioxanone), and poly(trimethylene carbonate).

6. A process for enhancing the security of implantable surgical devices secured to bone tissue comprising securing a surgical device to bone with a bioabsorbable semi-crystalline aliphatic poly(ester) copolymer composed of from about 100 mole percent to about 70 mole percent of ε-caprolactone repeating units with the remainder of the polymer being a plurality of second lactone repeating unit selected from the group consisting of glycolide repeating units, lactide repeating units, 1,4-dioxanone repeating units, 1,4-dioxepan-2-one repeating units, 1,5-dioxepan-2-one repeating units, trimethylene carbonate repeating units, and combinations thereof provided in an amount effective to increase the amount of force necessary to remove the implanted surgical device.

7. The process of claim 1 wherein the adhesive and/or sealant is applied to the implantable surgical device and the surgical device is then secured to the bone tissue.

8. An implantable surgical device consisting essential of an implantable surgical device that is at least partially coated with a biocompatible adhesive and/or sealant selected from the group consisting of:

(a) a bioabsorbable semi-crystalline aliphatic poly(ester) of the formula:

$$[-O-R^{11}-C(O)-]_y,$$

wherein $R^{11}$ is selected from the group consisting of $-CR^{12}H-$, $-(CH_2)_3-O-$, $-CH_2-CH_2-O-CH_2-$, $CR^{12}H-CH_2$, $-(CH_2)_4-$, $-(CH_2)_z-O-C(O)-$ and $-(CH_2)_z-C(O)-CH_2-$; $R^{12}$ is hydrogen or methyl; z is an integer in the range of from 1 to 7 and y is an integer in the range of from about 10 to about 20,000; and (b) a slurry of water and a calcium containing compound with the general formula:

$$M^{2+}{}_{10-n}N^{1+}{}_{2n}(WO_4{}^{3-})_6mU^{x-}$$

where n is an integer from 1 to 10, and m is 2 when x is 1, or m is 1 when x is 2, M and N are alkali or alkaline earth metals; $WO_4$ is an acid radical and W is phosphorus, vanadium, sulfur, silicon, or is substituted in whole or part with carbonate ($CO_3{}^{2-}$); and U is a halide, hydroxide, or carbonate; provided in an amount effective to increase the amount of force necessary to remove the implanted surgical device.

9. The surgical devices of claim 8 wherein the surgical device is selected from the group consisting of screws, pins, plates, anchors, rods, clamps, clips, staples, rivets, hooks, buttons and snaps.

10. The surgical device of claim 8 wherein the surgical device is made of a bioabsorbable polymeric material.

11. The surgical device of claim 8 wherein the adhesive and/or sealant that at least partially coats the surgical device is a bioabsorbable semi-crystalline aliphatic poly(ester) homopolymer selected from the group consisting of poly(ε-caprolactone), poly(p-dioxanone), and poly(trimethylene carbonate).

12. An implantable surgical device comprising an implantable surgical device that is at least partially coated with a bioabsorbable semi-crystalline aliphatic poly(ester) copolymer composed of from about 100 mole percent to about 70 mole percent of ε-caprolactone repeating units with the remainder of the polymer being a plurality of second lactone repeating units selected from the group consisting of glycolide repeating units, lactide repeating units, 1,4-dioxanone repeating units, 1,4-dioxepan-2-one repeating units, 1,5-dioxepan-2-one repeating units, trimethylene carbonate repeating units, and combinations thereof provided in an amount effective to increase the amount of force necessary to remove the implanted surgical device.

* * * * *